US00PP25323P3

(12) United States Plant Patent
Suphachadiwong

(10) Patent No.: US PP25,323 P3
(45) Date of Patent: Mar. 3, 2015

(54) *PHALAENOPSIS* PLANT NAMED 'SUPHAL1302'

(50) Latin Name: ***Phalaenopsis* hybrid**
Varietal Denomination: SUPHAL1302

(71) Applicant: Thumrong Suphachadiwong, Chonburi (TH)

(72) Inventor: Thumrong Suphachadiwong, Chonburi (TH)

(73) Assignee: Suphachatwong Innovation (TH)

( * ) Notice: Subject to any disclaimer, the term of this patent is extended or adjusted under 35 U.S.C. 154(b) by 35 days.

(21) Appl. No.: 13/815,826

(22) Filed: Mar. 15, 2013

(65) Prior Publication Data
US 2014/0283263 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell

(57) ABSTRACT

A new and distinct *Phalaenopsis* cultivar named 'SUPHAL1302' is disclosed, characterized by white flowers with red-purple apical and dorsal lobes as well as small leaf and flower size. The new variety is a *Phalaenopsis*, typically produced as an indoor ornamental plant.

2 Drawing Sheets

Figure 1:
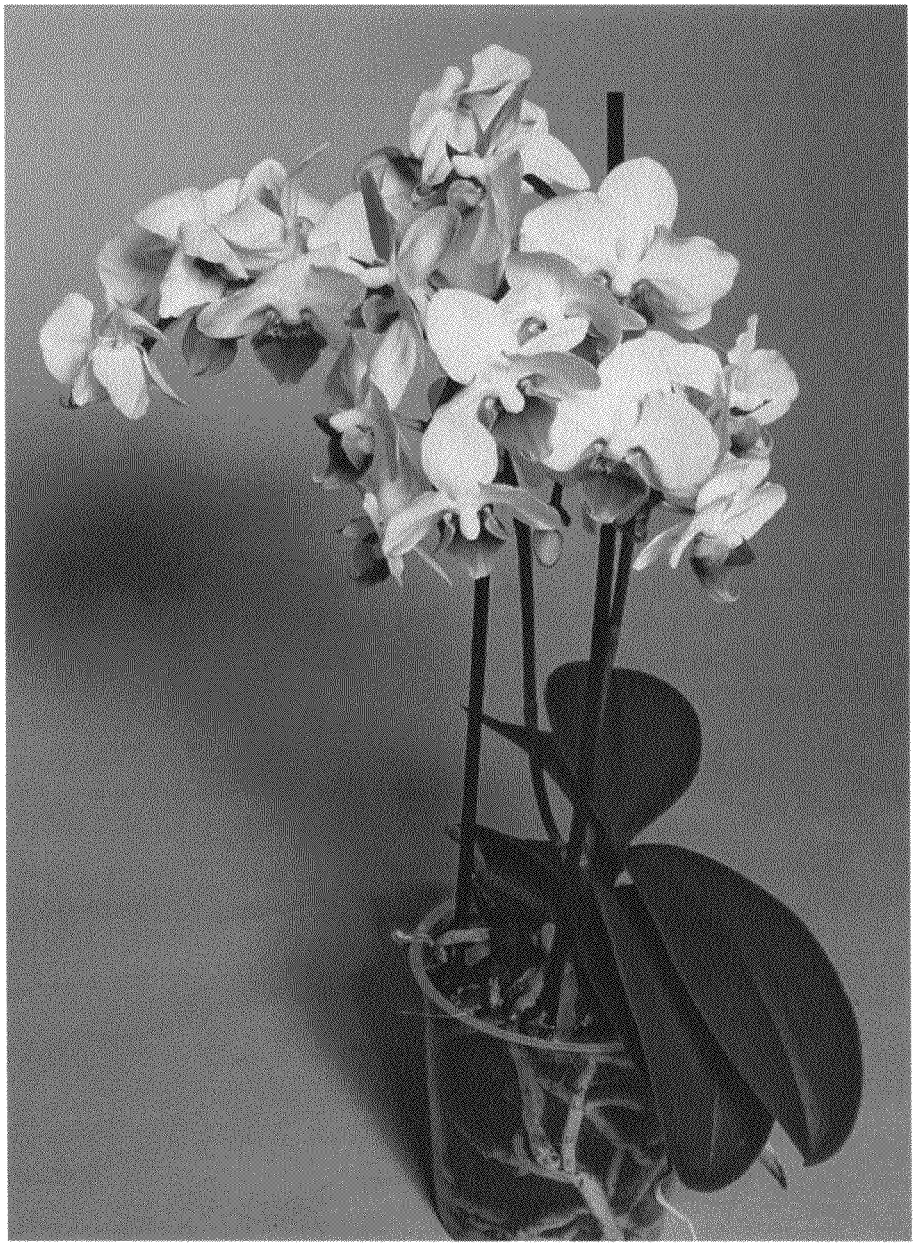

Latin name of the genus and species: *Phalaenopsis* hybrid. Variety denomination: 'SUPHAL1302'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'TP17PD' with the unpatented, proprietary pollen parent referred to as *Phalaenopsis* 'JWR5S'. The crossing was made by the inventor in his research greenhouse in Chonburi, Thailand in January of 2006.

The new variety was first selected by the inventor, Thumrong Suphachadiwong, a citizen of Thailand, in December of 2008 in a research greenhouse belonging to the inventor in Chonburi, Thailand. After identifying the new variety as a potentially interesting selection, the inventor continued confidential testing and propagation of 'SUPHAL1302', assessing stability of the unique characteristics of this variety.

Asexual reproduction of the new cultivar 'SUPHAL1302' was first performed at a commercial laboratory belonging to the inventor in Chonburi, Thailand by tissue culture in August of 2009. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1302' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1302'. These characteristics in combination distinguish 'SUPHAL1302' as a new and distinct *Phalaenopsis* cultivar:

1. White flowers with red-purple apical and dorsal lobes.
2. Small leaf size.
3. Small flower size.

PARENT COMPARISON

Plants of the new cultivar 'SUPHAL1302' are similar to the seed parent, *Phalaenopsis* 'TP17PD' in most horticultural characteristics. The new variety, however, produces a red-purple lip instead of the yellow one of the seed parent. Additionally the lateral petals are not as pure white as those of the seed parent.

Plants of the new cultivar 'SUPHAL1302' are similar to the pollen parent, *Phalaenopsis* 'JWR5S' in most horticultural characteristics. Plants of the new variety however produce a larger flower than the pollen parent.

COMMERCIAL COMPARISON

'SUPHAL1302' is similar in most horticultural characteristics to the unpatented variety *Phalaenopsis* 'SUPHAL1005'. However the new variety, 'SUPHAL1302' differs from 'SUPHAL1005' in the following characteristics:

1. Leaves are more upright.
2. Taller plant height.
3. Lateral and apical lobes are red-purple with a yellow base compared to the solid purple of 'SUPHAL1005'.
4. Different apical lobe shape.

BRIEF DESCRIPTION OF THE PHOTOGRAPHS

The accompanying photograph in FIG. 1 illustrates in full color a typical plant of 'SUPHAL1302' grown in a commercial greenhouse in Zuidbroek, the Netherlands. This plant is approximately 18 months old after deflasking, shown planted in an 11 cm container.

Figure 2:
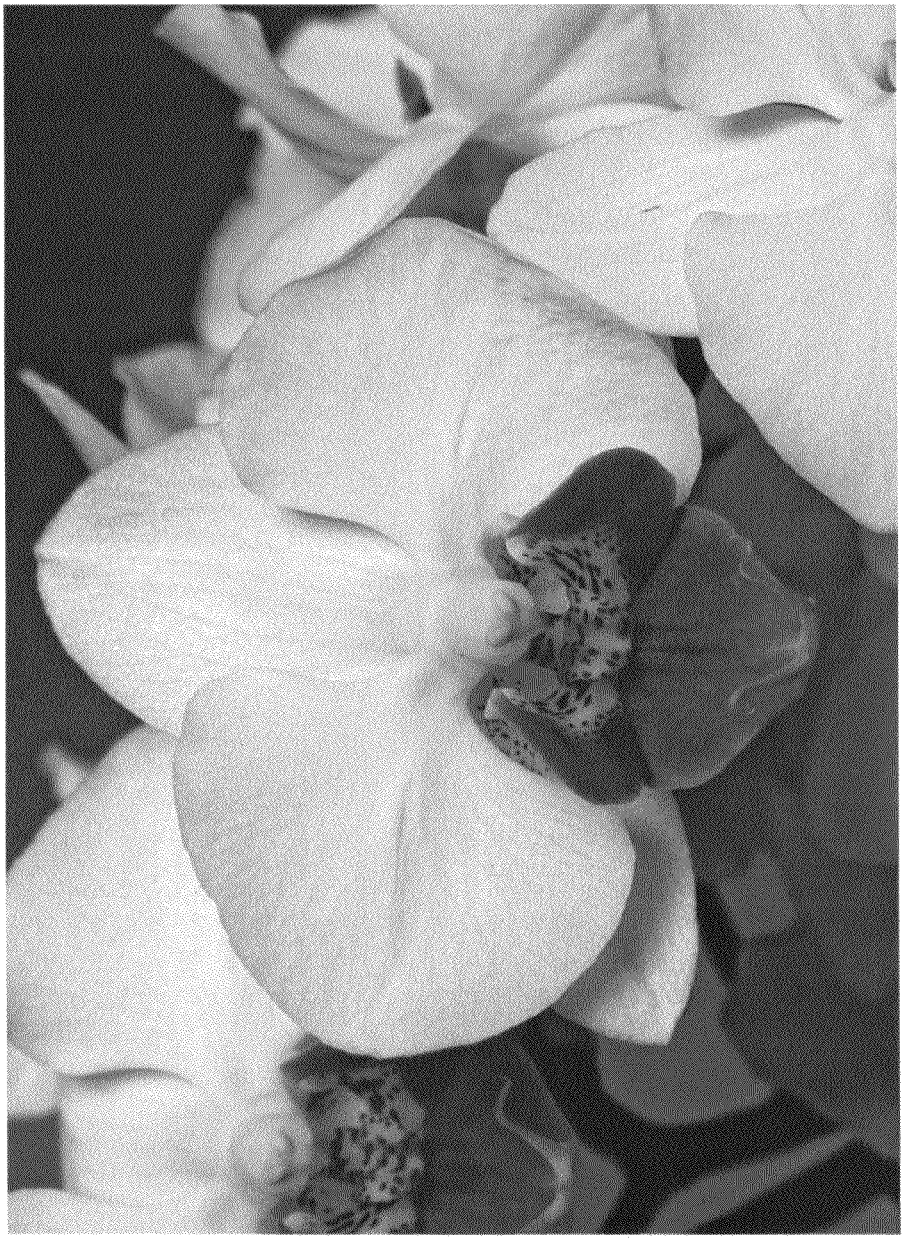

FIG. 2 illustrates a close up of the individual flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1302' plants grown in a commercial greenhouse in Zuidbroek, the Netherlands. This plant is approximately 18 months old after deflasking, shown planted in an 11 cm container. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1302'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 198D.

PLANT

Growth habit: Monopodial.

Height from top of soil line to top of foliage: Average 7.4 cm.

Height from top of soil line to top of flowers: Average 30.4 cm.

Plant spread: At widest, average: 25.0 cm; at narrowest: 24.0 cm.

Normal pot size: 11 cm.

Growth rate: Moderate.

Number of leaves per plant: Average 8.

FOLIAGE

Leaf:

- *Arrangement*.—Distichous.
- *Average length*.—Approximately 13.4 cm (including sheath).
- *Average width*.—Approximately 6.3 cm.
- *Shape of blade*.—Obovate.
- *Aspect*.—Horizontal to slightly curled downward.
- *Apex*.—Unequal acute, slightly pointed downward.
- *Base*.—Cuneate. Sheath length: Average 1.2 cm. Sheath width: Average 1.3 cm. Sheath color: Green to yellow-green; in between near RHS 143C and 146C.
- *Margin*.—Entire.
- *Texture of top surface*.—Smooth, very slightly furrowed.
- *Texture of bottom surface*.—Smooth.
- *Appearance of top surface*.—Glossy.
- *Appearance of bottom surface*.—Glossy.
- *Color*.—Young foliage upper side: Green; near RHS N137B. Young foliage under side: Yellow-green; near RHS 146A to 146B. Mature foliage upper side: Green; near RHS N137B. Mature foliage under side: Yellow-green; near RHS 146A to 146B.
- *Venation*.—Type: Camptodromous. Venation coloration: Upper side green; near RHS N137B, under side yellow-green; near RHS 146A to 146B, main vein on under side green; near RHS 137A.

Petiole: No petiole present.

FLOWERING CHARACTERISTICS

Flower bud:

- *Rate of opening*.—Approximately 3 days after stage described.
- *Length*.—Approximately 1.8 cm.
- *Diameter*.—Approximately 1.4 cm wide and 1.6 cm high.
- *Shape*.—Broad ovate.
- *Color*.—White; near RHS NN155C, striped and flushed purple; near 77B.

Peduncle:

- *Length*.—Approximately 33.6 cm.
- *Width*.—Approximately 0.4 cm.
- *Aspect*.—Approximately 60° angle to rosette.
- *Strength*.—Strong.
- *Texture*.—Smooth.
- *Appearance*.—Matte.
- *Color*.—Green; near RHS 137B.

Inflorescence:

- *Height*.—Average 12 cm.
- *Width*.—Average 18 cm.
- *Arrangement*.—Panicle.
- *Flowers per stem*.—Average range 8 to 12.

Individual flower:

- *Flower type*.—Single zygomorphic flower.
- *Shape*.—Rounded deltate.
- *Length* (*height*).—Approximately 5.2 cm.
- *Width*.—Approximately 5.6 cm.
- *Depth*.—Approximately 2.4 cm.
- *Fragrance*.—No fragrance.
- *Persistent*.—Non-persistent.
- *Quantity of petals*.—2 true petals.

Petals:

- *Arrangement*.—One petal on each side of the column.
- *Length*.—Approximately 2.5 cm.
- *Width*.—Approximately 3.2 cm.
- *Shape*.—Deltoid.
- *Apex*.—Rounded.
- *Base*.—Cuneate.
- *Margin*.—Entire.
- *Texture*.—Upper (forward) surface: Smooth, moderately velvety.
- *Texture*.—Lower (back) surface: Smooth, moderately velvety.
- *Appearance*.—Dull all surfaces.
- *Color*.—When opening, forward surface: White; near RHS NN155C, very slightly tinged purple; near RHS 77B. When opening, back surface: White; near RHS NN155C, very slightly tinged purple; near RHS 77B. Fully Opened, forward surface: White; near RHS NN155C, very slightly tinged purple; near RHS 77B.

Fully Opened, back surface: White; near RHS NN155C, very slightly tinged purple; near RHS 77B. Fading, forward surface: Not fading, only becoming non-velvety. Fading, back surface: Not fading, only becoming non-velvety.

*Color venation*.—Fully Opened, forward surface: As surface, white; near RHS NN155C, very slightly tinged purple; near RHS 77B. Fully Opened, back surface: As surface, white; near RHS NN155C, very slightly tinged purple; near RHS 77B.

Labellum:

*Shape*.—Three-parted.

*Length*.—Approximately 2.0 cm.

*Width*.—Approximately 2.2 cm.

*Texture*.—Smooth, slightly velvety.

*Appearance*.—Dull.

*Tip*.—Cleft, tips cirrhose, curled upward.

*Base*.—Cuneate.

*Color*.—When opening, forward surface: Central lobe red-purple; near RHS 72B, coloured lighter towards the top; near RHS 72C, lateral lobes red-purple; near RHS 72B, base white; near RHS NN155B, dotted greyed-red; near RHS 181A, callosities yellow; near RHS 8A and 8B, dotted grey-brown; near RHS 199A. When opening, back surface: Central lobe white; near RHS 155C, tinged red-purple to purple towards the margins; near RHS 72B and 77B, lateral lobes purple; near RHS 77B, base white; near RHS 155C. Fully Opened, forward surface: Central lobe red-purple; near RHS 72B, coloured lighter towards the top; near RHS 72C, lateral lobes red-purple; near RHS 72B, base white; near RHS NN155B, dotted greyed-red; near RHS 181A, callosities yellow; near RHS 8A to 8B, dotted grey-brown; near RHS 199A. Fully Opened, back surface: Central lobe white; near RHS 155C, tinged red-purple to purple towards the margins; near RHS 72B to 77B, lateral lobes purple; near RHS 77B, base white; near RHS 155C. Fading, forward surface: Not fading, only texture changes, becoming non-velvety. Fading, back surface: Not fading, only texture changes, becoming non-velvety.

*Color venation*.—Fully Opened, forward surface: No venation visible. Fully Opened, back surface: No venation visible.

*Margin*.—Entire.

Sepals:

*Quantity*.—3.

*Appearance*.—Matte.

*Length*.—Approximately 2.9 cm.

*Width*.—Dorsal sepal approximately 2.3 cm. Lateral sepals approximately 1.8 cm.

*Shape*.—Ovate.

*Apex*.—Broad bluntly acute.

*Base*.—Broad cuneate.

*Margin*.—Entire.

*Texture*.—Smooth, moderately velvety.

*Color*.—Fully Opened, forward surface: White; near RHS NN155C, lateral sepals dotted purple at the base; near RHS 77A. Fully Opened, back surface: White; near RHS NN155C, main vein tinged purple; near RHS 77A and 77B.

Pedicels:

*Length*.—Approximately 2.5 cm.

*Diameter*.—Approximately 0.2 cm.

*Angle*.—Approximately 85° to peduncle.

*Strength*.—Moderately strong.

*Texture*.—Smooth.

*Appearance*.—Moderately glossy.

*Color*.—Yellow-green; near RHS 145B, distal part white; near RHS N155C.

REPRODUCTIVE ORGANS

*Stamens, style and stigma fused into column*.—Yes.

*Column length*.—Approximately 0.8 cm.

*Column diameter*.—Approximately 0.5 cm.

*Column color*.—White; near RHS NN155D.

*Ovary*.—Position: Inferior. Diameter: Approximately 0.3 cm. Color: White; near RHS NN155D.

*Pollen color*.—Yellow-orange; near RHS 21A.

OTHER CHARACTERISITCS

Disease resistance: Neither resistance nor susceptibility to the normal diseases found in *Phalaenopsis* has been observed.

Drought tolerance and cold tolerance: Normal for species.

Fruit/seed production: No fruits/seeds detected to date.

What is claimed is:

1. A new and distinct cultivar of *Phalaenopsis* plant named 'SUPHAL1302' as herein illustrated and described.

* * * * *